United States Patent
Yamanaka et al.

[11] Patent Number: 5,830,497
[45] Date of Patent: Nov. 3, 1998

[54] MEDICATED PLASTER CONTAINING BASIC PHYSIOLOGICALLY ACTIVE AGENTS AND/OR SALTS THEREOF

[75] Inventors: Akihito Yamanaka; Takashi Kinoshita; Masaki Sunami, all of Osaka, Japan

[73] Assignee: Nitto Denko Corporation, Osaka, Japan

[21] Appl. No.: 655,007

[22] Filed: May 29, 1996

Related U.S. Application Data

[63] Continuation of Ser. No. 493,657, Mar. 15, 1990, abandoned.

[30] Foreign Application Priority Data

| Mar. 15, 1989 | [JP] | Japan | 1-64424 |
| Mar. 29, 1989 | [JP] | Japan | 1-79167 |
| May 31, 1989 | [JP] | Japan | 1-140047 |

[51] Int. Cl.$^6$ .............................. A61F 13/02; A61K 9/14
[52] U.S. Cl. ..................... 424/448; 424/449; 424/486; 424/487; 514/818; 514/821; 514/906; 514/929
[58] Field of Search ........................ 424/448, 449, 424/486, 487, 80, 81, 83; 514/818, 821, 907, 929

[56] References Cited

U.S. PATENT DOCUMENTS

| 4,690,683 | 9/1987 | Chien et al. |
| 4,738,848 | 4/1988 | Yoshida et al. |
| 4,740,374 | 4/1988 | Nakano et al. |
| 4,755,384 | 7/1988 | Mallasz |
| 4,765,974 | 8/1988 | Tokuda et al. |
| 4,814,174 | 3/1989 | Barta et al. |
| 4,888,354 | 12/1989 | Chang et al. |

FOREIGN PATENT DOCUMENTS

| 0276561 | 12/1987 | European Pat. Off. |
| 85318 | 5/1982 | Japan |
| 126809 | 7/1983 | Japan |
| 28917 | 2/1985 | Japan |
| 41968 | 3/1985 | Japan |
| 2156215 | 10/1985 | United Kingdom |

OTHER PUBLICATIONS

Japanese Abstract "Pharmaceutical Preparation of Drug for Endermic Administration" vol. 10, No. 49 (C–330) [2106] Feb. 26, 1986.

Japanese Abstract "Pharmaceutical Formulation for Percutaneous Administration" vol. 12, No. 306 (C–522) [3153] Aug. 19, 1988.

Primary Examiner—Thurman K. Page
Assistant Examiner—Kathryne E. Shelborne
Attorney, Agent, or Firm—Sughrue, Mion, Zinn, Macpeak & Seas, PLLC

[57] ABSTRACT

Medicated plasters composed of a flexible support and a pressure-sensitive adhesive layer laminated thereon, in which said pressure-sensitive adhesive layer has an exposed surface with pH of 7 or higher and contains one of the following three components:

i) a basic physiologically active agent and an acidic substance, ii) a salt of a basic physiologically active agent and a basic substance, and iii) a basic physiologically active agent and a salt of a basic physiologically active agent.

1 Claim, 9 Drawing Sheets

MEDICATED PLASTER CONTAINING BASIC PHYSIOLOGICALLY ACTIVE AGENTS AND/OR SALTS THEREOF

This is a continuation of application Ser. No. 07/493,657 filed Mar. 15, 1990 now abandoned.

FIELD OF THE INVENTION

This invention relates to medicated plasters containing, as active ingredient, a basic physiologically active agent and/or a salt thereof.

BACKGROUND OF THE INVENTION

Medicated plasters are known as a dosage form for percutaneous absorption.

Some of these employ, as the base material, a pressure-sensitive adhesive made of an elastomeric or acrylic polymer in order to ensure close adherance to the skin. Plasters of this type, however, are generally low in solubility for medicine. Particularly, it is extremely difficult to keep a medicine of salt form dissolved uniformly; even when prepared uniformly, the involved medicine tends to become crystallized during storage, thus discouraging its percutaneous absorption.

Techniques are known in which an organic acid is added to the pressure-sensitive adhesive layer containing a medicine for the purpose of, (X) improving the releasability of medicine and its percutaneous absorption (for example, Japanese Patent Kokai No. 79820/1988 and No. 126119/1987), and (Y) preventing the loss of medicine with the passage of time, thus ensuring its stable preservation over long periods (for example, Japanese Patent Kokai No. 193920/1985 and No. 100715/1981).

In any of these techniques, however, no attention is given to the pH of the exposed surface of pressure-sensitive adhesive layer.

The above technique (X) has the problem that the content of medicine frequently declines with the passage of time, and the technique (Y) suffers from poor releasability and percutaneous absorption of the involved medicine in some cases. Thus, plasters combining the features of techniqes (X) and (Y) have not been developed yet.

SUMMARY OF THE INVENTION

Intensive studies to solve the above problems have led us to find that plasters combining the features of techniques (X) and (Y) can be obtained, if one pays attention to whether the medicine to be involved in the pressure-sensitive adhesive layer is a free base or in the form of a salt and determines the necessity of an additive and the type of additive to be used, and if pH of the exposed surface of said adhesive layer is set at a level of 7 or higher. This invention was accomplished on the basis of these findings.

This invention relates to medicated plasters composed of a flexible support and a pressure-sensitive adhesive layer laminated thereon, said pressure-sensitive adhesive layer having an exposed surface with pH of 7 or higher and containing one of the following three components:

(i) a basic medicine and an acidic substance,
(ii) a salt of a basic medicine and a basic substance, and
(iii) a basic medicine and a salt of a basic medicine.

DETAILED DESCRIPTION OF THE INVENTION

The pressure-sensitive adhesive layer of this invention serves to hold a basic medicine, and/or a salt thereof and an acidic (and/or basic) substance and to ensure adhesion of the plaster to the skin.

Acrylic polymers are suitable materials for the pressure-sensitive adhesive layer of this invention in terms of adhesion to the skin and stability of the medicine involved therein.

As examples of the acrylic pressure-sensitive adhesive, there may be mentioned polymers composed of at least one alkyl (meth)acrylate having an akyl group of 4 to 13 carbon atoms [e.g., butyl (meth)acrylate, pentyl (meth)acrylate, hexyl (meth)acrylate, heptyl (meth)acrylate, octyl (meth)acrylate, nonyl (meth)acrylate, decyl (meth)acrylate, undecyl (meth)acrylate, dodecyl (meth)acrylate and tridecyl (meth)acrylate], and copolymers composed of at least one alkyl (meth)acrylate mentioned above and at least one copolymerizable monomer.

Examples of the copolymerizable monomer include the following:

(a) Carboxyl-containing monomers, such as (meth)acrylic acid, itaconic acid, crotonic acid, maleic acid, fumaric acid and maleic anhydride; and hydroxyl-containing monomers, such as hydroxyethyl (meth)acrylate and hydroxypropyl (meth)acrylate, (b) alkyl (meth)acrylates containing an ether linkage (or linkages) in the molecule, such as methoxyethyl (meth)acrylate, ethoxyethyl (meth)acrylate, butoxyedthyl (meth)acrylate, tetrahydrofurfuryl (meth)acrylate, methoxyethylene glycol (meth)acrylate, methoxydiethylene glycol (meth)acrylate, methoxypolyethylene glycol (meth)acrylate and methoxypolypropylene glycol (meth)acrylate,

(c) Monomers represented by the following general formula, (wherein R denotes hydrogen atom or methyl goup, and X stands for a radical having at least one nitrogen atom, or nitrogen and oxygen atoms), including (meth)acrylates containing an alkylaminoalkyl group, such as aminoethyl (meth)acrylate, dimethylaminoethyl (meth)acrylate, diethylaminoethyl (meth)acrylate, and tert-butyl (meth)acrylate; and functional acrylic monomers, such as esters of (meth) acrylic acid with urethane, urea and isocyanates.

(d) Monomers represented by the following general formula, $$CH_2=CH-X$$

(wherein X denotes a radical having at least one nitrogen atom, or nitrogen and oxygen atoms), including vinyl monomers carrying a saturated or unsaturated N— containing heterocyclic ring (such as vinylcaprolactam, vinylimidazole, vinylmethylimidazole, vinylphenylimidazole, vinylpyrrolidone, vinylmethylpyrrolidone, vinylpiperidone, vinylpyridine, vinylpiperadone, vinylpyrimidine, vinyloxazole, acryloylmorpholine, vinylmorpholine, vinylthiazole, vinylpyrazine, vinylpiperazine and vinylpyrrole); acrylic monomers containing an amide group [such as (meth)acrylamide, diemthyl(meth)acrylamide, N-butylacrylamide, tetramethylbutylacrylamide and N-meth-ylol-(meth)acrylamide]; and vinyl monomers such as N-(meth)acryloylamino acids.

(e) Vinyl monomers, such as (meth)acrylonitrile, vinyl acetate, vinyl propionate, vinyloxazole, styrene, α-methylstyrene and bis(N,N'-dimethylaminoethyl) maleate; and sulfoxy-containing monomers, such as styrenesulfonic acid, allylsulfonic acid, sulfopropyl acrylate, (meth)acryloyloxynaphthalenesulfonic acid, acrylamidomethylpropanesulfonic acid and acryloyloxybenzenesulfonic acid.

The above-mentioned alkyl (meth)acrylates and the copolymerizable monomers also include isomers containing linear or branched alkyl groups, isomers in which substituent groups are located at different positions, and various derivatives thereof.

Of the monomeric compounds mentioned above, combinations of an alkyl (meth)acrylate with (meth)acrylic acid are preferable in terms of high polymerizability as well as high cohesion and adhesion of resulting copolymers. Vinyl acetate is preferable in terms of high cohesion of resulting copolymers.

The weight ratio of an alkyl (meth)acrylate to a copolymerizable monomer should preferably be in the range of 50~99/50~1 to ensure a good balance between cohesion and adhesion to the skin. When an alkyl (meth)acrylate containing an ether linkage (or linkages) in the molecule is used to minimize irritation to the skin, the weight ratio between an alkyl (meth)acrylate, an alkyl (meth)acrylate containing an ether linkage (or linkages) and a third copolymerizable monomer should preferably be 40~80/59~10/1~40. In this case, use of vinyl acetate as the third copolymerizable monomer is preferable in terms of high cohesion of resulting copolymers. "The third copolymerizable monomer" means the monomers other than the above mentioned monomers.

When a water-soluble and latently basic monomer of group (c) and/or (d) is used to ensure good adhesion to the skin as well as high solubility and releasability of medicine, the weight ratio of alky(meth) acrylates to said water-soluble monomer should preferably be 50~96/50~4, more preferably 60~90/10~30.

When said monomer of group (c) and/or (d) is used, a polar monomer of group (a) can be further included in the copolymer in an amount up to 20 weight %. This serves to improve cohesion, adhesion to the skin and hydrophilic nature.

Use of vinylpyrrolidone as a monomer of group (c) and/or (d) helps improve cohesion and hydrophilic nature, and use of hydroxyethyl (meth)acrylate as a polar monomer of group (a) serves to improve hydrophilic nature.

As examples of pressure-sensitive adhesives of other type, may be mentioned elastomeric polymers (such as silicone rubber, polyisoprene rubber, polyisobutylene rubber, polybutadiene rubber, styrene-butadiene(or isoprene)-styrene block copolymers and natural rubber), vinyl polymers (such as polyvinyl alkyl ethers, polyvinyl acetate and a partially saponified product thereof, polyvinyl alcohol and polyvinylpyrrolidone), cellulose derivatives (such as methylcellulose, carboxymethylcellulose and carboxypropylcellulose) polysaccharides (such as pullulan, dextrin and agar) polyurthane elastomers, and polyester elastomers.

When the pressure-sensitive adhesive used is low in cohesion and part of it is left attached to the skin after peeling off the plaster it is preferred that the polymer composition be subjected to proper chemical crosslinking (copolymerization with a crosslinkable monomer or addition of an external crosslinker) or to physical crosslinking application of ionizing radiations, such as electron rays or ultraviolet crosslinking) to such a moderate degree as not to adversely affect the adhesion to the skin.

As the support to hold the above mentioned pressure sensitive adhesive layer may be used a flexible material that can follow the movements of skin surface such as plastic film, nonwoven fabrics, woven fabrics, paper, metallic foil, and laminated products thereof.

Basic medicines and the salts thereof used in this invention are those which are physiologically acceptable; particularly those which contain at least one amino or amide group (of any type) in the molecule are preferred. The term "base" herein means a Lewis base defined by the Lewis theory ("Valence and the Structure of Atoms and Molecules" 1923 Gilbert N. Lewis); hence. the basic medicines mean those containing a Lewis base (or bases) in the molecule. "Physiologically acceptable" means that that medicine can be safely administered to human bodies. Such basic medicines may be divided into two groups — systemic drugs (those acting systemically, with the active ingredient involved working into blood vessels), and local drugs (those acting locally, with no need of the active ingredient working into blood vessels) —, and medicines of both types are applicable in this invention.

Salts of these basic medicines may be of any types ( both organic and inorganic), such as citrates, succinates, fumarates, maleates, tartrates, hydrochlorides, sulfates and phosphates.

Listed below are illustrated examples of the salt-form basic medicines to be used in this invention.

(1) Hypnotic and Sedative Agents

Flurazepam hydrochloride, etc.

(2) Antipyretic, Analgesic and Antiphlogistic Agents

Cinnolidine hydrochloride, benzidamine hydrochloride, perisoxisal citrate, refetamine hydrochloride, tramadole hydrochloride, dimethothiazine mesylate, buprenorfin hydrochloride, butorphanol tartrate, etc.

(3) Stimulating and Antihyptonic Agents

Methanefetamine hydrochloride etc.

(4) Anti-emetics

Meclizine hydrochloride, dl-isoprenaline hydrochloride, diphenidol hydrochloride, betahistine mesylate, etc.

(5) Medicines for Psyconeurosis

Phenothiazine compounds: chlorpromazine hydrochloride, chlorpromazine hibenzate, triflupromazine hydrochloride. levomepromazine maleate, levomepromazine hydrochloride, perazine maleate, perazine phendizoate, prochlorperazine maleate, trifloperazine maleate.

thioridazine hydrochloride pulphenazine phendizoate, perphenazine maleate, pulphenazine hydrochloride, fluphenazine maleate, fluphenazine hudrochloride, spiclomazine hydrochloride, etc.

Compounds of phenothiazine-like skeletal structure: Flupentixol hydrochloride, etc.

Butyrophenone compounds: floropipamide hydrochloride, moperone hydrochloride, etc.

Diphenylmethane compounds: Hydroxydine hydrochloride, etc.

Carpipramine compounds: carpipramine hydrochloride, carpipramine maleate, clocapramine hydrochloride. etc.

Tricyclic antidepressants: imipramine hydrochloride, desipramine hydrochloride, trimipramine maleate, clomipramine hydrochloride, amitriptyline hydrochloride, nortriptyline hydeochloride, dosulepin hydrochloride, melitracene hydrochloride, lophepramine hydrochloride, etc.

Tetracylic antidepressants: mianserin hydrochloride, maprotiline hydrochloride, etc.

MAO inhibitors: safrazine hydrochloride, etc.

Benzodiazepine compounds: chlordiazepoxide hydrochloride, etc.

Others: methylphenidate hydrochloride, pipradrol hydrochloride, etc.

(6) Skeletal Muscle Relaxants

Pridinol mesylate, eperison hydrochloride, tolperison hydrochloride, etc.

(7) Antispasmodics

Choline blockers: atropine sulfate, scopolamine hydrobromide, dicyclomine hydrochloride, pipethanate hydrochloride, piperidolate hydrochloride, oxyphencyclimine hydrochloride, methixene hydrochloride, etc.

Others: papaverine hydrochloride, etc.

(8) Antiparkinsonism Agents

Piperidene hydrochloride, piperidene lactate. trihexyphenidyl hydrochloride, amantadine hydrochloride, pyroheptin hydrochloride, profenamine hibenzate, profenamine hydrochloride, mazathicol hydrochloride, etc.

(9) Antihistaminics

Ethanolamine compounds: diphenhydramine hydrochloride, diphenhydramine salicylate, carbinoxamine maleate, etc. Monoamine compounds: dl-chlorphenilamine maleate, d-chlorphenilamine maleate, etc.

Phenothiazine compounds: alimemazine tartrate, etc.

Others: isotipendyl hydrochloride, triprolidine hydrochloride, clemizole hydrochloride, cyploheptadine hydrochloride, homochlorcyclizine hydrochloride, diphenylpyraline hydrochloride, iproheptin hydrochloride, dimethindene maleate, clemastine fumarate. etc.

(10) Cardiotonics dl-Isoproterenol hydrochloride, l-isoproterenol hydrochloride, dopamine hydrochloride, dobutamine hydrochloride, metaraminol tartrate, etilefrin hydrochloride, norfenefrine hydrochloride, etc.

(11) Medicines for Arrhythmia

Procainamide compounds: procainamide hydrochloride. etc.

Xylidine compounds: lidocaine hydrochloride. etc.

Kinidin compounds: kinidin sulfate, etc.

β-Blocking agents: metoprolol tartrate, propranolol hydrochloride, alprenolol hydrochloride, bufetolol hydrochloride, bupranolol hydrochloride, oxprenolol hydrochloride, indenolol hydrochloride, cartheolol hydrochloride/ befnolol hydrochloride, aceptolol hydrochloride, bukumolol hydrochloride, timolol maleate, alotinolol hydrochloride, etc.

Others: disopyramide phosphate. mexiretin hydrochloride. verapamil hydrochloride. aprindine hydrochloride. etc.

(12) Hypotensive Agents

Hydralazine compounds: ekarazine hydrochloride, hydralazine hydrochloride, etc.

Alkaliods: dihydroergotoxine mesylate. etc.

Others: guanfacine hydrochloride, clonidine hydrochloride, bunazosine hydrochloride, bnitrolol hydrochloride, prazosin hydrochloride, propranolol hydrochloride, ravetalol hydrochloride, guanabenze acetate enallapril maleate, guanethidine sulfate, betanidine sulfate, penbutolol sulfate, etc.

(13) Vasoconstrictors

Phenylephrine hydrochloride, methoxamine hydrochloride, dihydroergotamine mesylate, etc.

(14) Coronary Vessel Vasodilators

Etafenone hydrochloride. oxyfedrine hydrochloride, dilazep hydrochloride, diltiazem hydrochloride, trimetadizine hydrochloride, verapamyl hydrochloride, carbochromen hydrochloride, prenylamine lactate, etc.

(15) Peripheral Vessel Vasodilators

Isoxsuprine hydrochloride, nicametate citrate, nicotinic alcohol tartrate, bamethan sulfate. trazoline hydrochloride, etc.

(16) Medicines for Other Circulatory Organs

Nikaldipine hydrochloride, ifenprodil tartrate, pirithioxine hydrochloride, flunaridine hydrochloride, meclofenoxate hydrochloride, moxisylate hydrochloride. brovincamine fumarate, bencyclane fumarate, cinepazide maleate, thiapride hydrochloride, etc.

(17) Respiration Accelerators

Lobeline compounds: lobeline hydrochloride, etc.

Dimorpholamine compounds: levallorphan tartrate, etc.

Others: dimefline hydrochloride, doxapram hydrochloride, naloxone hydrochloride, etc.

(18) Antitussives and Expectorants

Centrally acting antitussives: codeine phosphate, dihydrocodeine phosphate, dextromethorphan hydrobromide, carbetapentane citrate, benproperine phosphate, tipepidine hibenzate, isoaminile citrate, dimemorfan phosphate, oxeladin citrate, evradinone hydrochloride, clobutinol hydrochloride, clofedanol hydrochloride, fominoben hydrochloride, etc.

Other antitussives: noscapine hydrochloride, etc. Expectorants: L-ethylcysteine hydrochloride, L-methylcysteine hydrochloride, bromhexine hydrochloride, amproxcl hydrochloride, etc.

Sympathetic nerve stimulants: dl-epinephrine hydrochloride, ephedrine hydrochloride, dl-methylephedrine hydrochloride, 1-methylephedrine hydrochloride, isoproterenol sulfate, dl-isoproterenol hydrochloride, orciprenaline sulfate, terbutaline sulfate, salbutanol sulfate, trimetoquinol hydrochloride, clorprenaline hydrochloride, methoxyphenamine hydrochloride, hexoprenaline sulfate, bitolterol mesylate, procaterol hydrochloride, tulobuterol hydrochloride, pirbuterol hydrochloride, fenoterol hydrobromide, formoterol, fumarate, clenbuterol hydrochloride, mabuterol hydrochloride, etc.

Antiallergic agents: ketotiphen fumarate, azerastine hydrochloride, etc.

(19) Hormones

Clomifene citrate, etc.

(20) Medicines for suppurative diseases (for external use

Mafenide acetate, etc.

(21) Analgesic, Antipruritic, Astringent and Antiphlogistic Agents

Isothipendyl hydrochloride, etc.

(22) Medicines for Parasitic Dermatosis

Miconazole nitrate, econazole nitrate, iconazole nitrate, sconazole nitrate, oxyconazole nitrate, cloconazole hydrochloride. etc.

(23) Vitamins

Vitamin $B_1$ compounds: dicethiamine hydrochloride, cycothiamine hydrochloride, etc.

(24) Hemostatics

Adrenochromeguanylhydrazone mesylate, etc.

(25) Blood Clotting Inhibitors

Ticropydine hydrochloride. etc.

(26) Toxicides and Medicines for Habitual Intoxication Deferoxamine Mesylate, etc.

(27) Medicines for Diabetes

Methoformin hydrochloride, buformin hydrochloride, etc.

(28) Medicines for Malignant Tumors

Alkylating agents: nitrogen mustard N-oxide hydrochloride. isoprosulfan tosylate, nimstine hydrochloride, etc.

Antimetabolytes: ancitavine hydrochloride, etc.

Plant alkaloids: vinblastine sulfate, vincristine sulfate, vindesine sulfate, etc.

Cancerocidal antibiotics: daunorubicin hydrochloride, doxorubicin hydrochloide, etc.

Others: tamoxifen citrate, procarbazine hydrochloride, etc.

(29) Narcotics

Opiate alkaloids: ethylmorphine hydrochloride, morphine hydrochloride, codeine phosphate, dihydrocodeine phosphate, etc.

Coca alkaloids: cocaine hydrochloride, etc.

Synthetic narcotics: pethidine hydrochloride, phentanyl citrate, etc.

The above-mentioned basic medicines and/or salts thereof may be used in physiologically effective amounts, which are generally in the range of 20 to 5000 $\mu g/cm^2$, preferably 100 to 4000 $\mu/cm^2$, per unit area of pressure-sensitive adhesive layer. Amounts lower than 20 $\mu g/cm^2$ frequently fail to exhibit satisfactory physiolosical effects, while amounts higher than 5000 $\mu g/cm^2$ do not show higher effects and cause skin irritation and other troubles in some cases. Normally, these active ingredients are included in pressure-sensitive adhesive in amounts of 0.1 to 50 weight %, preferably 1 to 30 weight %.

Conventional pressure-sensitive adhesives are generally low in solubility for medicines; particularly, it is extremely difficult to keep a medicine of salt form dissolved uniformly. Even when kept dissolved uniformly, the salt-form medicine involved is scarcely released in many cases. It is true that medicines of free form can be easily kept dissolved uniformly and released satisfactorily in most cases, compared with those of salt form, but the problem is that the content of medicine tends to decline in some cases as a result of its change with the passage of time during storage.

In this invention, these problems are avoided by using a pressure-sensitive adhesive layer having an exposed surface with pH of 7 or higher and containing a composition of a basic medicine, a salt thereof, an acidic substance and a basic substance as shown in (i), (ii) and (iii) above.

So long as the pH is kept at a level of 7 or higher, an acidic or basic substance may be added to the adhesive layer as required. The pH of exposed surface herein means the value measured by the use of a flat electrode; pH of waterdrops put on the exposed surface when it nearly comes to equilibrium (when the pH value remains unchanged for at least 30 seconds). Since water cannot be included in the pressure-sensitive adhesive layer, the acidic and basic substances added do not serve as so called pH regulator. Unless the pH of exposed surface is 7 or higher, the medicine involved cannot be released sufficiently to the skin surface and hence its satisfactory percutaneous absorption cannot be achieved.

The above-mentioned composition (i) contains an acidic substance, and the compositions (ii) and (iii) each contain a salt of a basic medicine which carries an acid group in the molecule. Hence, an acid is contained besides a basic medicine in each of the compositions, and said acid is effective in preventing the decline of medicine content caused by its change with the passage of time.

Any acidic substances that are physiologically acceptable in terms of safety may be used for this purpose, but use of organic acids (particularly carboxylic acids) is preferred. Typical examples include citric, succinic tartaric, maleic, fumaric, benzoic, salicylic and lactic acids.

The basic substances to be added should be those which are more basic than the medicine used and are physiologically acceptable in terms of safety. These include inorganic bases, such as sodium hydroxide and potassium hydroxide; amines, such as triethanolamine, diethanolamine, triisopropanolamine and diisopropanolamine; and basic amino acids such as arginine. Scuh basic substances serve to form a free-base medicine from its salt; thereby facilitating the release of medicine.

The suitable amounts of these acidic and basic substances are 0.1 to 10 moles, preferably 0.5 to 5 moles, per mole of the medicine or its salt used.

The above-mentioned problems associated with conventional plasters can be overcome by the existense of an acid, and a basic substance in the pressure-sensitive adhesive layer. The reason for the foregoing is not absolutely clear yet but it is believed that some intermolecular forces interact in the pressure-sensitive adhesive layer among the functional groups of the adhesive components, the acid or basic group eliminated from the acidic and/or basic substance, and the free-base physiologically active agent (and an acid) formed from the basic physiologically active agent and/or a salt thereof. These intermolecular forces differ from those observed in solutions in the mechanism by which they work and in their strength and include forces of various types including, for example, those not observed in solutions and those weaker than in solutions. Presumably, these intermolecular forces serve to eliminate the above-mentioned problems.

As is apparent from the foregoing, the medical plasters of this invention containing a basic medicine and/or a salt thereof feature high releasability of active ingredient and its high percutaneous absorption, with no decline of medicine content caused by its change with the passage of time.

The following examples will further illustrate the invention, but are not intended to limit its scope (various modifications of these examples may be made). The parts shown in these examples are all expressed on a weight basis.

Preparative Example 1

In a four-necked flask were placed 55 parts of 2-ethylhexyl acrylate, 30 parts of methoxyethyl acrylate, 15 parts of vinyl acetate and 0.3 part of azobisisobutyronitrile, the mixture was heated to a temperature of 60° to 63° C. in an inert gas atmosphere to start polymerization, the reaction was continued for ten hours while adjusting the temperature by dropwise addition of 125 parts ethyl acetate, and heating was further continued for two hours at a temperature of 75° to 80° C. to complete the reaction, giving a solution of a pressure-sensitive adhesive.

Preparative Example 2

In a four-necked flask were placed 95 parts of 2-ethylhexyl acrylate, 5 parts of acrylic acid and 0.2 part of bezoyl peroxide, the mixture was heated to a temperature of 62° to 65° C. in an inert gas atmosphere to start polymerization, the reaction was continued for eight hours while adjusting the temperature by dropwise addition of 125 parts ethyl acetate, and heating was further continued for two hours at a temperature of 75° to 80° C. to complete the reaction, giving a solution of a pressure-sensitive adhesive.

Preparative Example 3

In a four-necked flask were placed 80 parts of isononyl acrylate, 15 parts of 1-vinyl-2-pyrrolidone, 5 parts of 2-hydroxyethyl methacrylate and 66.7 parts of ethyl acetate in an inert gas atmosphere, 0.2 part of azobisisobutyronitrile was added as polymerization initiator, the mixture was heated at a temperature of 62° to 65° C. for seven hours with stirring while adjusting the temperature by dropwise addition of 190.4 parts ethyl acetate, and heating was further continued for three hours at a temperature of 75° to 80° C. to complete the reaction, giving a solution of a pressure-sensitive adhesive.

Preparative Example 4

Three kinds of polyisobutylenes —35 parts VISTANEX MML-80 (product of Exxon Chemicals Co. Ltd.; viscosity-average molecular weight: 990000), 15 parts HIMOL 4H (product of Nippon Petrochemicals Co. Ltd.; viscosity-average molecular weight: 40000) and 50 parts HV-300 (product of Nippon Petrochemicals Co. Ltd.; viscosity-average molecular weight: 1260)—were dissolved in 50 parts toluene, giving a solution of a pressure-sensitive adhesive.

Preparative Example 5

In a four-necked flask were placed 95 parts of 2-ethylhexyl acrylate and 5 parts of acrylic acid, 42.9 parts of ethyl acetate and 0.3 part of azobisisobutyronitrile were further added, the mixture was heated to 65° C. in an inert gas atmosphere to start polymerization, the reaction was continued for 18 hours while maintaining the temperature at 65° to 67° C. by addition of 107.1 parts ethyl acetate in small portions, and heating was further continued for ten hours at higher temperatures to complete the reaction, giving a solution of an acrylic pressure-sensitive adhesive.

Preparative Example 6

VISTANEX MML-80 (25 parts) and HIMOL-4H (75 parts) were dissolved in hexane, giving a solution of a pressure-sensitive adhesive (solid content: 25 wight %).

Examples 1 through 34, Comparative Examples 1 through 27

Plasters as listed in Tables 1 to 6 were prepared by using the copolymer solutions obtained in the above Preparative Examples 1 to 6. After adding each of the components to a copolymer solution in a prescribed amount, the resulting solution was coated on a polyester liner 75 μm thick and dried, and the dried coating was transferred onto a support listed below.

Examples 1–8, 29, 32–34, Comparative Examples 1–5, 23, 24, 27 —polyester film 9 μm thick Examples 9–12, 21–28, 31, Comparative Examples 6–9, 19–22—polyethylene film 30 μm thick Examples 13–16, Comparative Examples 10–13—polyester film 9 μm thick with ethylene-vinyl acetate copolymer film 20 μm thick (vinyl acetate content: 28 weight %) laminated thereon (transferred on the ethylene-vinyl acetate copolymer side)

Examples 17–20, Comparative Examples 14–18—polyester film 12 μm thick

Example 30, Comparative Examples 25,26—polyester film 6 μm thick with ethylene-vinyl acetate copolyner film 50 μm thick (vinyl acetate content: 28 weight %) laminated thereon (transferred on the ethylene-vinyl acetate copolymer side)

Characteristic features of the medicated plasters obtained in the above Examples and Comparative Examples are shown in Tables 1 to 6 and in FIGS. 1 to 9.

TABLE 1

| | Copolymer Solution* | Additive/Content (weight %) 1 | 2 | 3 | Active Agent ($\mu g/cm^2$) | Surface pH | Release Rate (%) |
|---|---|---|---|---|---|---|---|
| (Examples) | | | | | | | |
| 1 | A | Dopamine.HCl/10 | Triethanolamine/8 | — | 400 | 10.5 | 54.2 |
| 2 | B | Dopamine.HCl/30 | NaOH/7 | — | 1200 | 10.9 | 61.5 |
| 3 | C | Dopamine.HCl/20 | Triethanolamine/16 | — | 1000 | 10.2 | 52.2 |
| 4 | D | Dopamine.HCl/3 | Triethanolamine/2.5 | — | 400 | 11.0 | 58.3 |
| 5 | A | Dopamine/10 | Citric acid/2 | — | 400 | 8.8 | 47.1 |
| 6 | A | Dopamine.HCl/10 | Tartaric acid/8 | KOH/4 | 400 | 7.3 | 41.5 |
| 7 | B | Dopamine/20 | Citric acid/4 | Triethanolamine/30 | 800 | 9.5 | 50.9 |
| 8 | A | Dopamine.HCl/10 | Dopamine/10 | NaOH/2 | 800 | 10.3 | 54.1 |
| (Comparative Examples) | | | | | | | |
| 1 | A | Dopamine.HCl/10 | — | — | 400 | 5.1 | 8.2 |
| 2 | A | Dopamine.HCl/10 | Triethanolamine/0.05 | — | 400 | 6.3 | 10.1 |
| 3 | B | Dopamine.HCl/10 | Citric acid/6 | — | 800 | 4.4 | 5.1 |
| 4 | A | Dopamine/20 | Triethanolamine/10 | — | 1000 | 11.1 | 59.2 |
| 5 | A | Dopamine/20 | — | — | 400 | 10.7 | 55.6 |

*A: Pressure-sensitive adhesive solution obtained in Preparative Example (1)
B: Pressure-sensitive adhesive solution obtained in Preparative Example (2)
C: Pressure-sensitive adhesive solution obtained in Preparative Example (3)
D: Pressure-sensitive adhesive solution obtained in Preparative Example (4)

TABLE 2

| | Copolymer Solution* | Additive/Content (weight %) 1 | 2 | 3 | Active Agent ($\mu g/cm^2$) | Surface pH | Release Rate (%) |
|---|---|---|---|---|---|---|---|
| (Examples) | | | | | | | |
| 9 | A | Bunitrolol.HCl/15 | Triethanolamine/8 | — | 1200 | 9.1 | 45.4 |
| 10 | B | Bunitrolol.HCl/30 | NaOH/4 | — | 2400 | 9.3 | 43.2 |
| 11 | A | Bunitrolol/15 | Citric acid/2 | — | 1200 | 8.5 | 40.1 |
| 12 | A | Bunitrolol/20 | Fumaric acid/4 | Triethanolamine/5 | 1600 | 8.8 | 40.9 |
| (Comparative Examples) | | | | | | | |
| 6 | A | Bunitrolol.HCl/15 | — | — | 1200 | 5.7 | 4.7 |
| 7 | B | Bunitrolol.HCl/30 | Tartaric acid/10 | — | 2400 | 4.8 | 3.2 |
| 8 | A | Bunitrolol/20 | KOH/1 | — | 1200 | 9.2 | 46.2 |
| 9 | B | Bunitrolol/30 | — | — | 2400 | 9.0 | 42.0 |

*A: Pressure-sensitive adhesive solution obtained in Preparative Example (1)
B: Pressure-sensitive adhesive solution obtained in Preparative Example (2)

TABLE 3

| | Copolymer Solution* | Additive/Content (weight %) 1 | 2 | 3 | Active Agent ($\mu g/cm^2$) | Surface pH | Release Rate (%) |
|---|---|---|---|---|---|---|---|
| (Examples) | | | | | | | |
| 13 | A | Cinepazide maleate/10 | NaOH/1 | — | 800 | 8.5 | 33.6 |
| 14 | C | Cinepazide maleate/10 | KOH/2 | — | 1000 | 8.8 | 32.8 |
| 15 | A | Cinepazide/10 | Salicylic acid/2 | — | 1600 | 7.9 | 30.5 |
| 16 | A | Cinepazide/10 | Maleic acid/1.5 | NaOH/0.5 | 800 | 8.0 | 31.5 |
| (Comparative Examples) | | | | | | | |
| 10 | A | Cinepazide maleate/10 | — | — | 800 | 6.0 | 2.5 |
| 11 | A | Cinepazide meleate/10 | Tartaric acid/1 | — | 800 | 5.2 | 2.1 |
| 12 | C | Cinepazide/10 | Triethanolamine/1 | — | 1600 | 8.8 | 35.3 |
| 13 | A | Cinepazide/10 | — | — | 800 | 8.7 | 32.9 |

*A: Pressure-sensitive adhesive solution obtained in Preparative Example (1)
B: Pressure-sensitive adhesive solution obtained in Preparative Example (2)

TABLE 4

| | Copolymer Solution* | Additive/Content (weight %) 1 | 2 | 3 | Active Agent ($\mu g/cm^2$) | Surface pH | Release Rate (%) |
|---|---|---|---|---|---|---|---|
| (Examples) | | | | | | | |
| 17 | A | Clomifene citrate/20 | KOH/2 | — | 800 | 8.2 | 29.6 |
| 18 | B | Clomifene citrate/30 | Diethanolamine/15 | — | 1200 | 7.8 | 26.5 |
| 19 | A | Clomifene/20 | Lactic acid/4 | — | 1200 | 8.2 | 30.1 |
| 20 | A | Clomifene/10 | Succinic acid/3 | L-arginine/1 | 800 | 8.1 | 32.3 |
| (Comparative Examples) | | | | | | | |
| 14 | A | Clomifene citrate/20 | — | — | 800 | 5.6 | 2.1 |
| 15 | A | Clomifene citrate/20 | Tartaric acid/2 | — | 800 | 4.6 | 1.1 |
| 16 | B | Clomifene/20 | Citric acid/6 | — | 1200 | 6.1 | 7.3 |
| 17 | A | Clomifene/10 | Triethanolamine/1 | — | 1000 | 8.3 | 32.7 |
| 18 | A | Clomifene/20 | — | — | 800 | 8.4 | 31.5 |

*A: Pressure-sensitive adhesive solution obtained in Preparative Example (1)
B: Pressure-sensitive adhesive solution obtained in Preparative Example (2)

TABLE 5

| | Copolymer Solution* | Additive/Content (weight %) 1 | 2 | 3 | Active Agent ($\mu g/cm^2$) | Surface pH | Release Rate (%) |
|---|---|---|---|---|---|---|---|
| (Examples) | | | | | | | |
| 21 | A | Ifenprodil tartrate/5 | Triethanolamine/2 | — | 200 | 7.9 | 15.3 |
| 22 | A | Ifenprodil tartrate/5 | Triethanolamine/1 | — | 200 | 7.6 | 18.1 |
| 23 | A | Ifenprodil tartrate/5 | Triethanolamine/4 | — | 200 | 8.4 | 21.8 |
| 24 | A | Ifenprodil tartrate/5 | Triethanolamine/8 | — | 200 | 8.5 | 26.4 |
| 25 | A | Ifenprodil tartrate/5 | KOH/1 | — | 200 | 8.4 | 21.5 |
| 26 | A | Ifenprodil/5 | Citric acid/0.5 | — | 200 | 8.0 | 16.1 |
| 27 | A | Ifenprodil tartrate/20 | Triethanolamine/8 | — | 200 | 8.1 | 39.5 |
| 28 | E | Ifenprodil tartrate/20 | Triethanolamine/8 | — | 200 | 7.6 | 16.1 |
| (Comparative Examples) | | | | | | | |
| 19 | A | Ifenprodil tartrate/5 | — | — | 200 | 4.7 | 3.0 |
| 20 | A | Ifenprodil tartrate/5 | Triethanolamine/0.2 | — | 200 | 6.3 | 5.9 |
| 21 | A | Ifenprodil tartrate/5 | Citric acid/2 | — | 200 | 3.8 | 6.3 |
| 22 | A | Ifenprodil/5 | — | — | 200 | | |

*A: Pressure-sensitive adhesive solution obtained in Preparative Example (1)
B: Pressure-sensitive adhesive solution obtained in Preparative Example (2)

TABLE 6

| | Copolymer Solution* | Additive/Content (weight %) 1 | 2 | 3 | Active Agent ($\mu g/cm^2$) | Surface pH | Release Rate (%) |
|---|---|---|---|---|---|---|---|
| (Examples) | | | | | | | |
| 29 | A | Metorpolol tartrate/20 | Triethanolamine/9 | — | 1600 | 9.6 | 92.3 |
| 30 | B | Metorpolol tartrate/30 | NaOH/6 | — | 2000 | 10.9 | 86.5 |
| 31 | F | Metorpolol tartrate/5 | L-arginine/1 | — | 800 | 10.1 | 88.0 |
| 32 | A | Metoprolol/20 | Salicylic acid/3 | — | 1600 | 9.3 | 82.7 |
| 33 | A | Metoprolol/20 | Succinic acid/8 | Triethanolamine/10 | 2000 | 10.2 | 81.4 |
| 34 | A | Metopolol/20 | Metoprolol tartrate/10 | — | 2000 | 10.0 | 81.5 |
| (Comparative Examples) | | | | | | | |
| 23 | A | Metoprolol tartrate/30 | — | — | 1600 | 5.0 | 21.3 |
| 24 | A | Metoprolol/20 | — | — | 1600 | 10.7 | 93.2 |
| 25 | A | Metoprolol tartrate/20 | Tartaric Acid/4 | — | 1600 | 4.8 | 20.1 |
| 26 | B | Metoprolol/30 | Triethanolamine/5 | — | 2000 | 10.8 | 91.1 |
| 27 | A | Metoprolol/20 | Succinic acid/8 | Triethanolaamine/0.1 | 2000 | 6.7 | 39.5 |

*A: Pressure-sensitive adhesive solution obtained in Preparative Example (1)
B: Pressure-sensitive adhesive solution obtained in Preparative Example (2)
F: Pressure-sensitive adhesive solution obtained in Preparative Example (6)

The characteristics shown in Tables 1 to 6 and in FIGS. 1 to 9 were measured by the methods described below.

Surface pH (Tables 1 to 6)

The plasters obtained in Examples 1 to 34 and in Comparative Examples 1 to 27 were each cut into a round piece of 12 mmø, the liner was then peeled off, 0.1 ml of distilled water was added dropwise to the exposed surface, and pH of the applied water was measured until it came nearly to equilibrium (when the pH value remained unchanged for at least 30 seconds). The values shown in the tables are averages of four measurements.

Release Rate to the Skin (Tables 1 to 4, and 6)

Round test pieces of 30 mmø prepared from the plasters obtained in Examples 1 to 20, 29 to 34 and in Comparative Examples 1 to 18, 23 to 27 were each put on the grained back of a rabbit for eight hours, the medicine left therein was measured by extraction with methanol, and the rate of apparent release based on the original content was calculated. The values shown in the tables are average of three measurements.

Release Rate to the Skin (Table 5)

Test pieces of 35 mm×40 mm in size prepared from the plasters obtained in Examples 21 to 28 and in Comparative Examples 19 to 22 were each put on a human back for 15 hours, the ifenprodil tartrate or ifenprodil left therein was measured by extraction with methanol, and the rate of apparent release based on the original content was calculated. The values shown in the tables are averages of three measurements.

Figure 1:
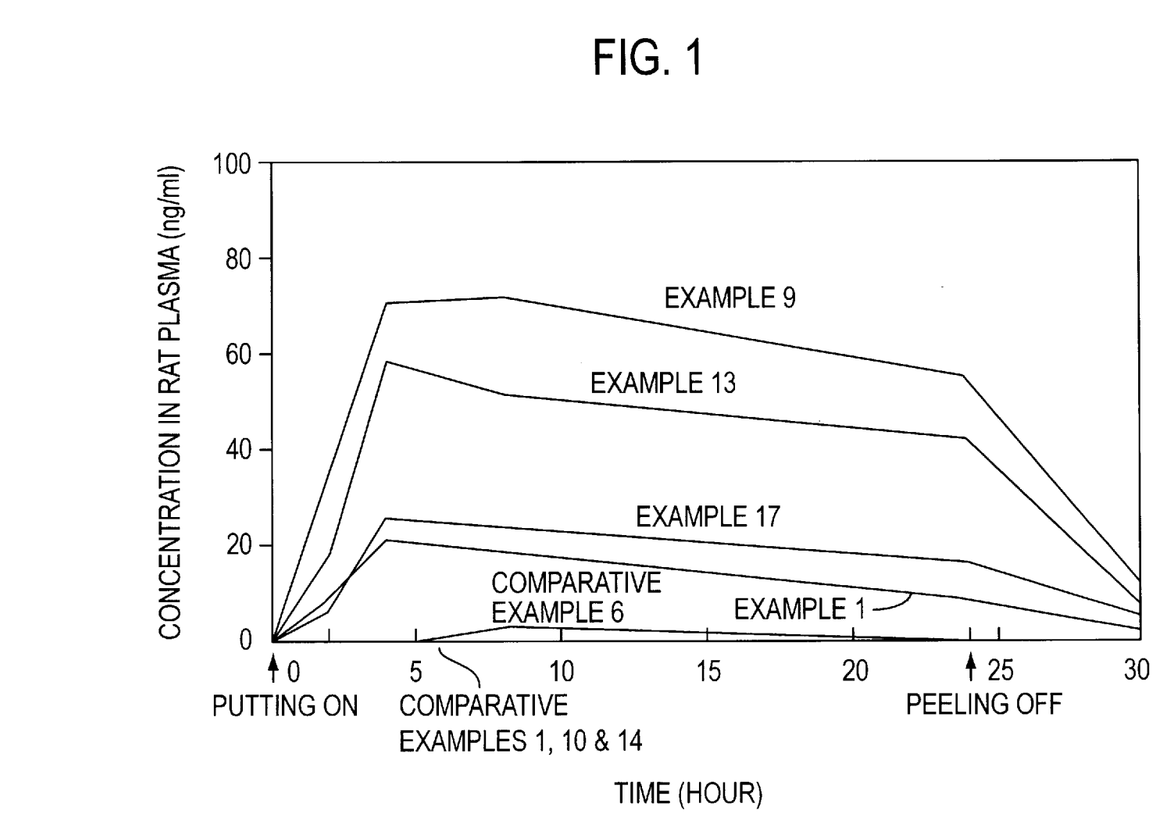
FIG. 1 shows characteristic, curves illustrating the concentration change in plasma with the passage of time for the medicines of Examples 1, 9, 13 and 17 and of Comparative Examples 1, 6, 10 and 14.
Figure 2:
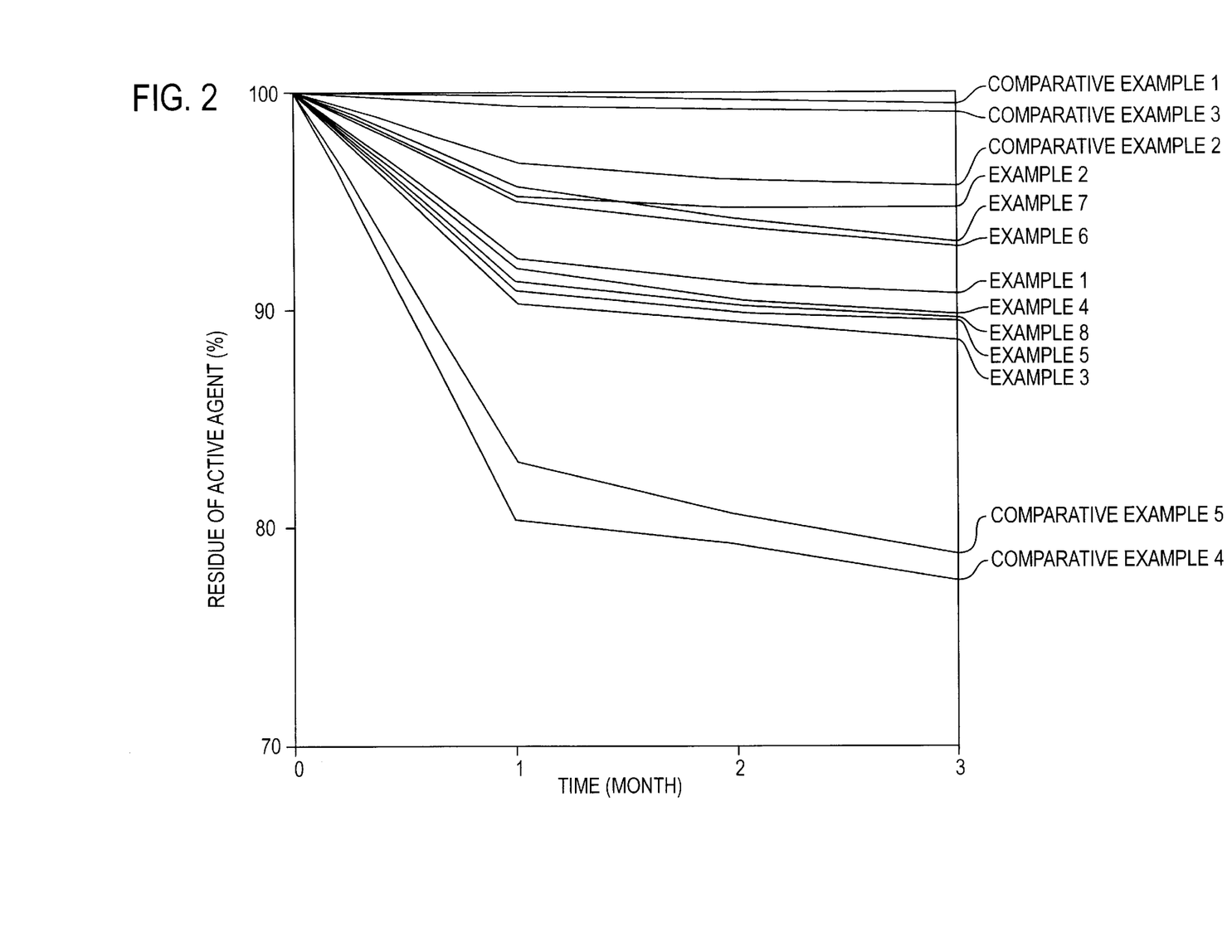
FIGS. 2, 3, 4 and 5 show characteristic curves illustrating the release rates for the medicines of Examples 1~8 and Comparative Examples 1~5, for the medicines of Examples 9~12 and Comparative Examples,6~9, for the medicines of Examples 13~16 and Comparative Examples 10~13, and for the medicines of Examples 17~20 and Comparative Examples 14~18, respectively.
Figure 3:
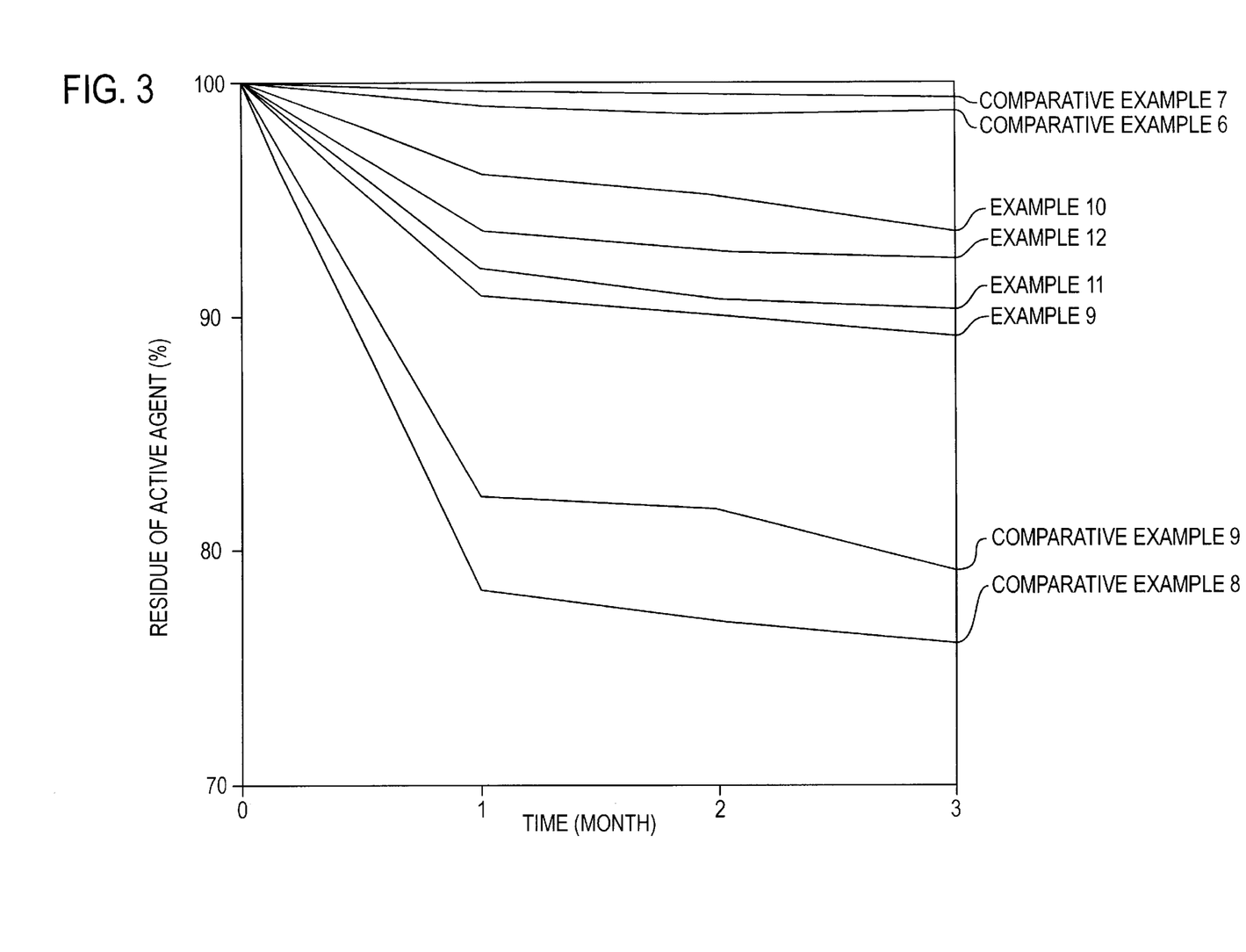
Figure 4:
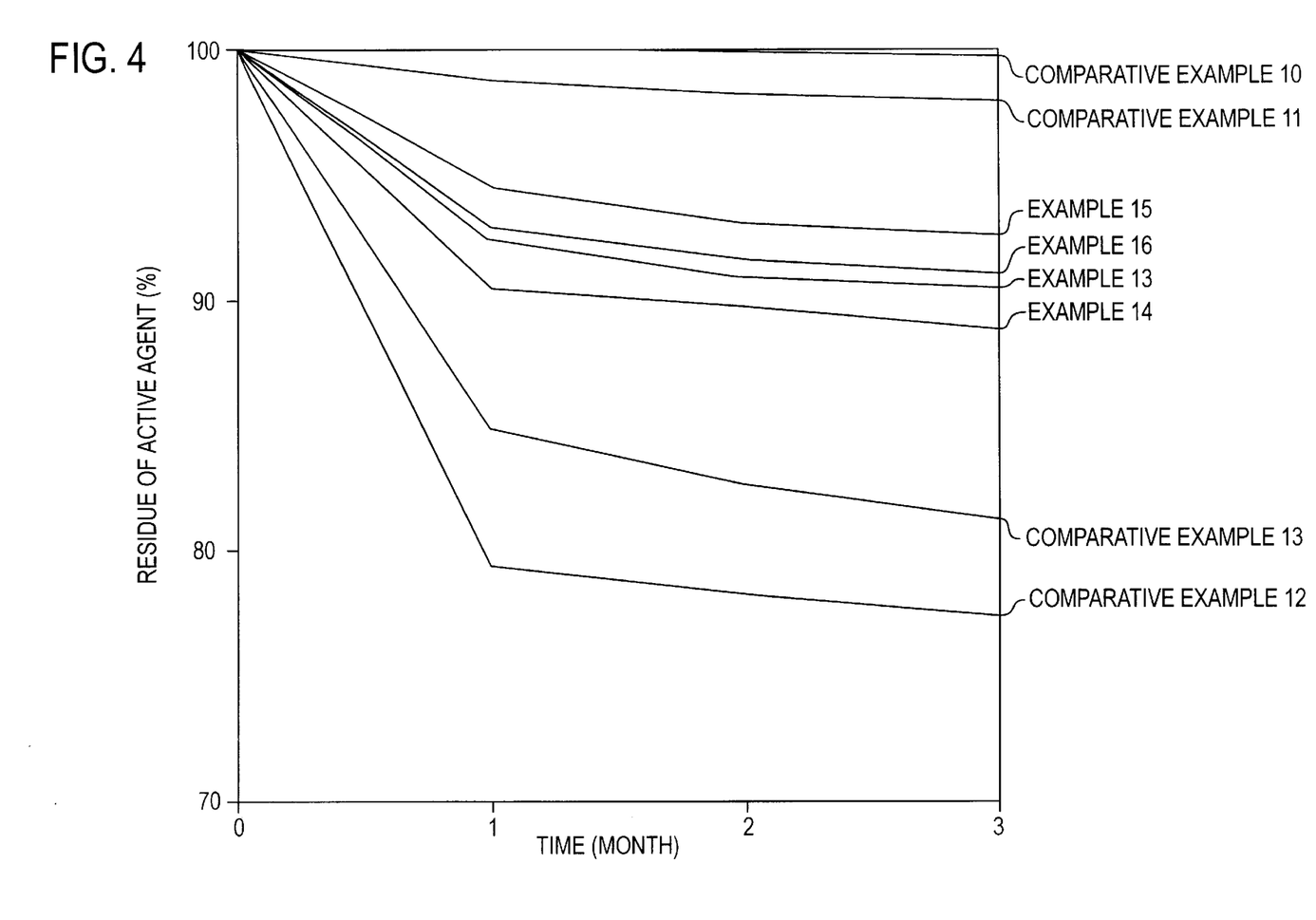
Figure 5:
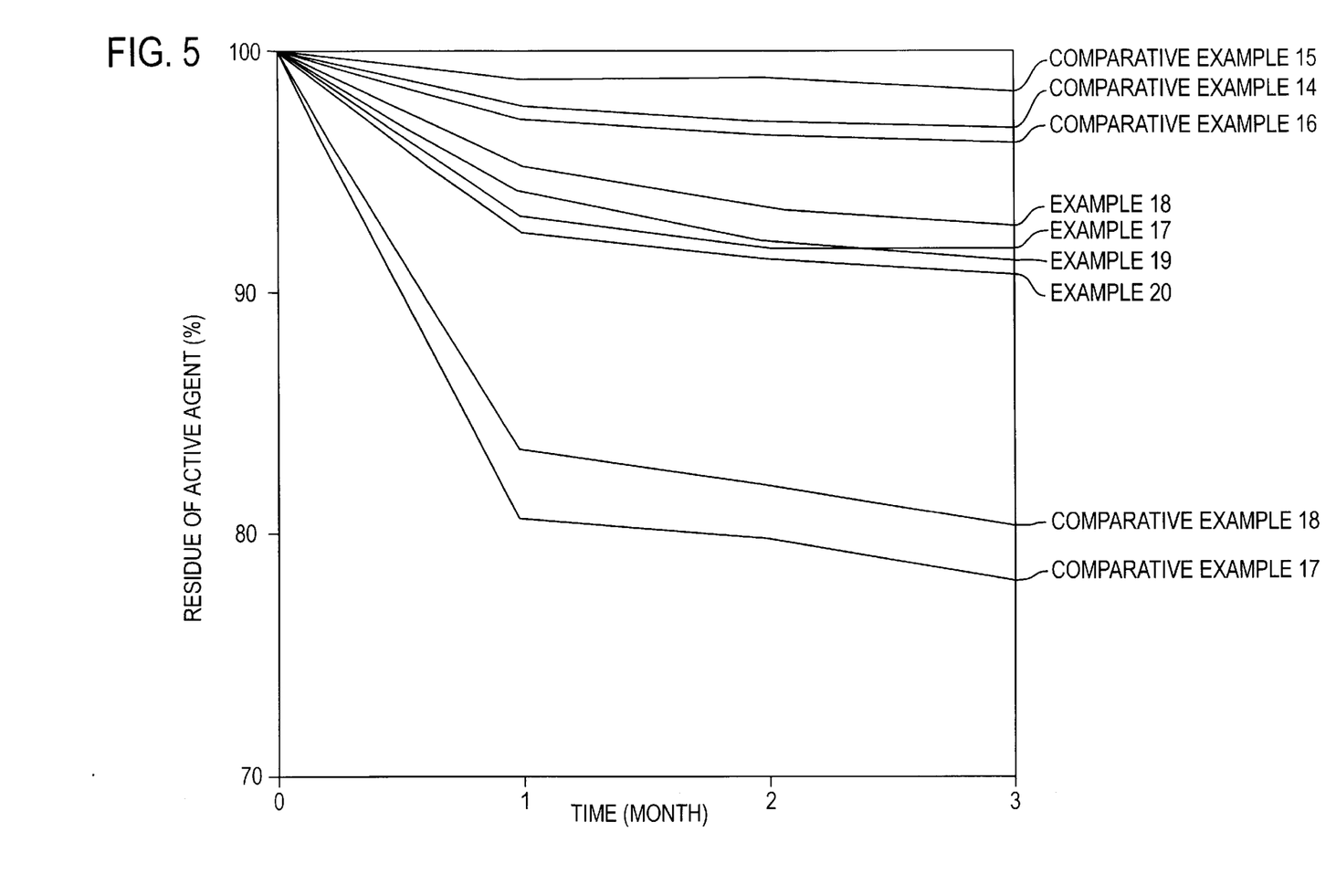

Concentration in Rat Plasma (FIG. 1)

(Dopamine Hydrochloride)

The plaster obtained in Example 1 was cut into a test piece with such a size that the dose of dopamine hydrochloride will be 1 mg per Kg of rat body weight. The test piece thus prepared was put on the grained back of rat and peeled off 24 hours later. Plasma samples were taken out 2, 4, 8, 24 and 30 hours after plaster application, and the medicine concentration in each sample was measured by the usual method. The values shown in FIG. 1 are averages of three measurements.

A similar test was carried out with the plaster obtained in Comparative Example 1, and the result obtained is also shown in FIG. 1.

(Bunitrolol Hydrochloride)

The plaster obtained in Example 9 was cut into a test piece with such a size that the dose of bunitrolol hydrochloride will be 10 mg per Kg rat body weight, and tested in the same way as with dopamine hydrochloride. The result obtained is shown in FIG. 1.

A similar test was carried out with the plaster obtained in Comparative Example 6, and the result is also shown in FIG. 1.

(Cinepazide Maleate)

The plaster obtained in Example 13 was cut into a test piece with such a size that the dose of cinepazide maleate will be 5 mg per Kg rat body weight, and tested in the same way as with dopamine hydrochloride. The result obtained is shown in FIG. 1.

A similar test was carried out with the plaster obtained in Comparative Example 10, and the result is also shown in FIG. 1.

(Clomifene Citrate)

The plaster obtained in Example 17 was cut into a test piece with such a size that the dose of clomifene citrate will be 1 mg per Kg rat body weight, and tested in the same way as with dopamine hydrochloride. The result obtained is shown in FIG. 1.

A similar test was carried out with the plaster obtained in Comparative Example 14, and the result is also shown in FIG. 1.

Concentration in Human Plasma

Figure 6:
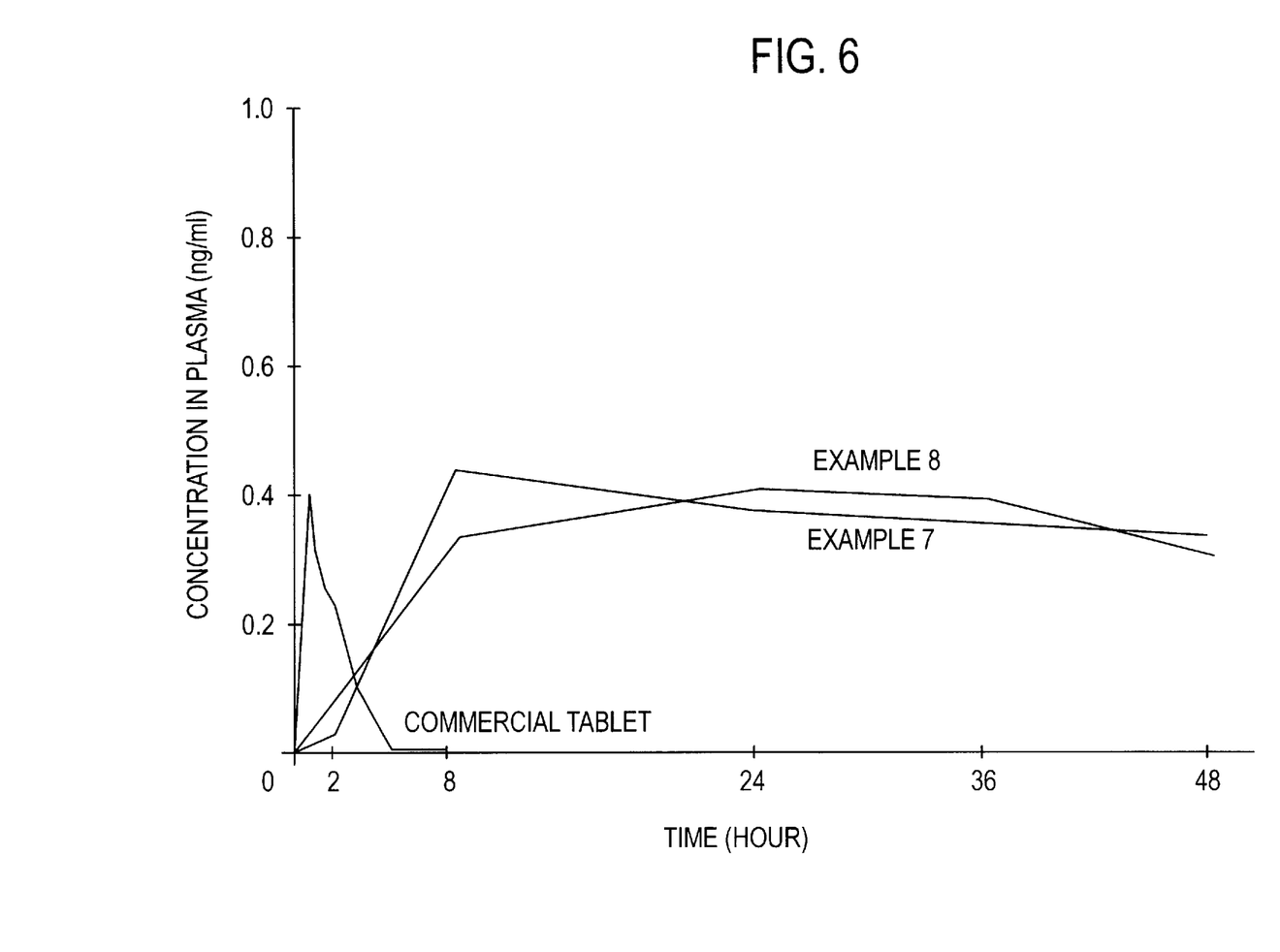
FIG. 6 shows characteristic curves illustrating the concentration change in plasma with the passage of time for the medicines of Examples 27 and 28 and for an oral medicine for comparison.

The plasters obtained in Examples 27 and 28 were cut into test pieces with such a size that the amount of medicine involved in each piece will be 40 mg, the pieces were put on the upper part of human backs (four subjects), and the medicine concentration in plasma was measured by GC-MS 2, 8, 24, 36 and 48 hours later. The detection limit of this method is 200 pg per ml plasma. FIG. 6 shows graphs illustrating the averages of measurements obtained.

The similar test result obtained when commercial tablets (active ingredient: 20 mg each) were orally administered is also shown in FIG. 6

Concentration in Beagle Plasma

The plasters obtained in Examples 29, 30 and 33 and in Comparative Example 23 and 24 were cut into test pieces with such a size that the amount of medicine involved in each piece will be 50 mg, the pieces thus prepared were put on the grained beagle backs, and the concentration of metoprolol in plasma was measured by HPLC 2, 3, 4, 6, 9, 12, 15, 24, 36 and 48 hours later.

Three beagles were used for each test group. The averages of measurements obtained are shown in FIG. 8.

Residue of Active Agent

The plasters obtained in Examples 1 to 21, 29 to 34 and in Comparative Examples 1 to 18, 22 to 27 were stored at 50° C. for one, two and three months, and then cut into round samples of 30 mmø. The amount of medicine left in each sample was measured by exctration with methanol or ethanol, and the residue based on the orignal content was calculated. The result obtained is shown in FIGS. 2 to 5, 7 and 9. The values in these figures are averages of two measurements.

Figure 8:
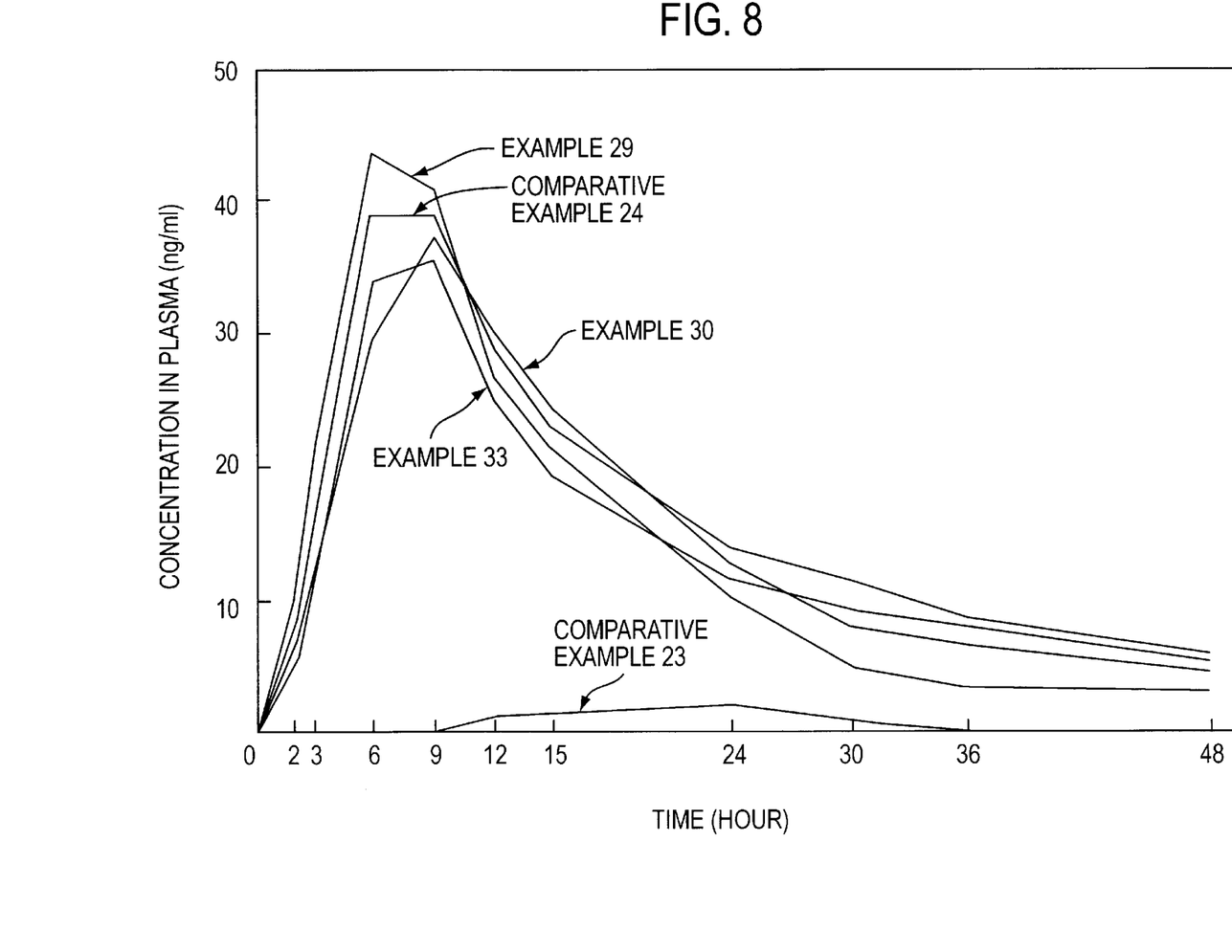
FIG. 8 shows characteristic curves illustrating the concentration change in plasma with the passage of time for the medicines of Examples 29, 30 and 33 and of Comparative Examples 23 and 24.
Figure 9:
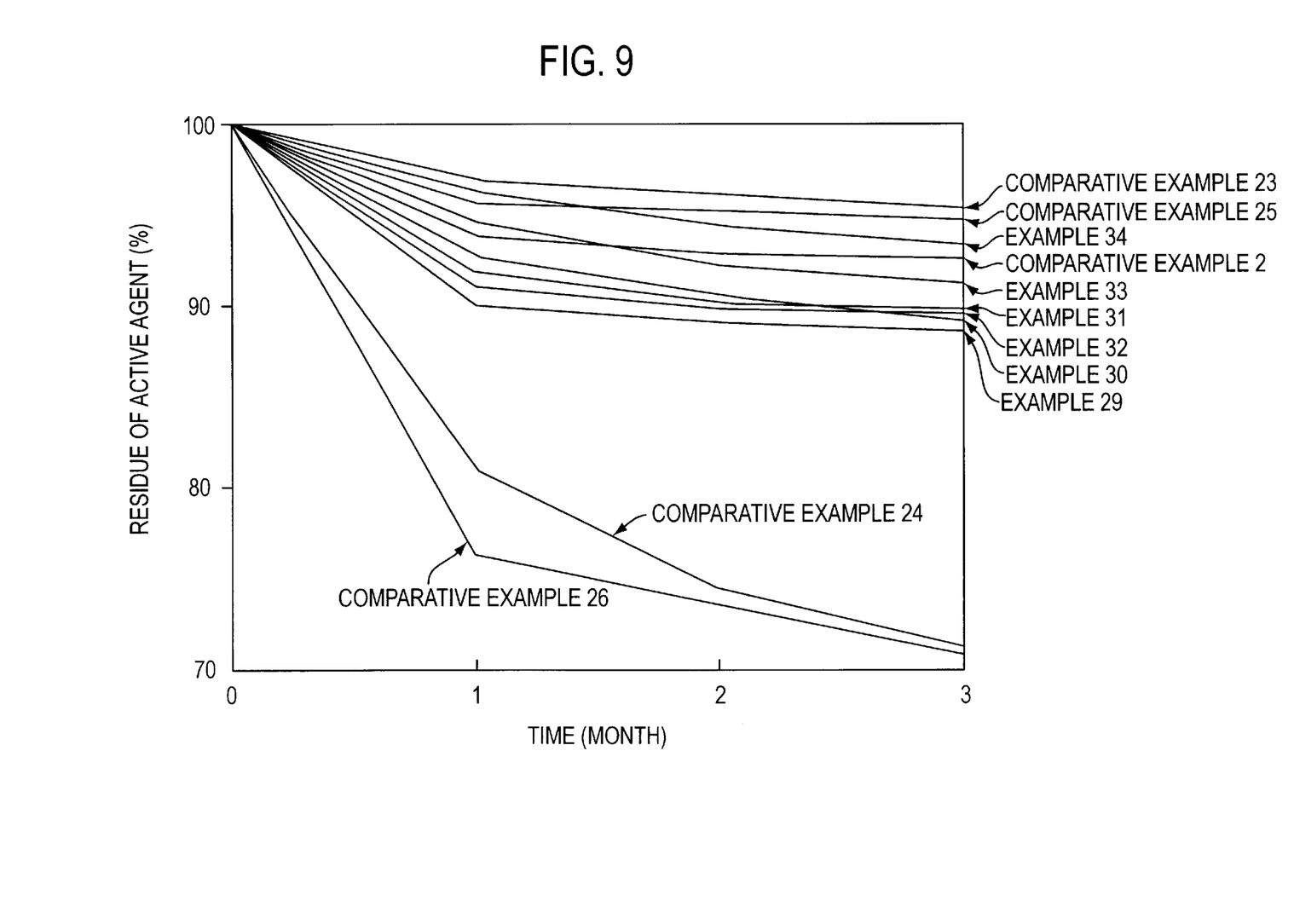
FIG. 9 shows characteristic curves illustrating the release rates for the medicines of Examples 29~34 and of Comparative Examples 23~27.

It is apparent from FIGS. 1 and 8 that the plasters obtained in Examples show higher concentration in plasma and are stored stably for longer periods, compared with those of Comparative Examples. FIG. 6 also shows that the plasters obtained in Examples 27 and 28 are higher concentration in plasma and are stored stably for longer periods, compared with commercial tablets.

Figure 7:
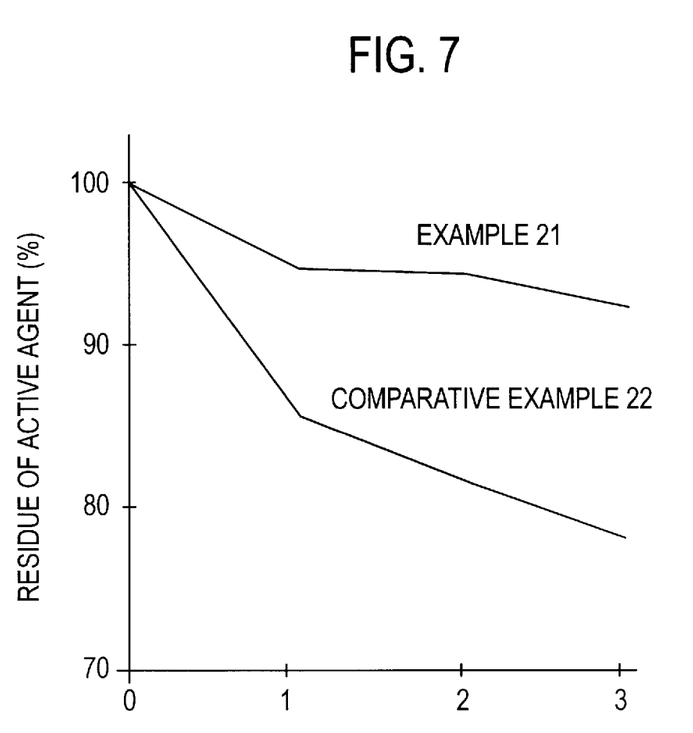
FIG. 7 shows characteristic curves illustrating the release rates for the medicines of Example 21 and Comparative Example 22.

FIGS. 2 to 5, and 9 show that the plasters obtained in Examples are higher in residue of involved medicine, compared with those of Comparative Examples 4, 5, 8, 9, 12, 13, 17, 18, 24 and 26 (which show high migration rate to the skin), indicating high stability in the pressure-sensitive adhesive layer. FIG. 7 also shows that the plaster obtained in Example 21 is higher in residue of involved medicine than that of Comparative Examples 22, indicating enhanced stability in the pressure-sensitive adhesive layer.

What is claimed is:

1. A medicated plaster composed of a flexible support and a pressure-sensitive adhesive layer laminated thereon, said pressure-sensitive adhesive layer having an exposed surface with pH of 7 or higher and containing one of the following three components in an amount from 20 to 5,000 $\mu g/cm^2$:

(i) a basic physiologically active agent and an acidic substance, (ii) a salt of a basic physiologically active agent and a basic substance, and (iii) a basic physiologically active agent and a salt of a basic physiologically active agent, wherein said basic physiologically active agent and/or a salt of said basic physiologically active agent is selected from the group consisting of metoprolol, ifenprodil, dopamine, bunitrolol, cinepazide, clomifene, eperison, propranolol, enalapril, ketotifen, lidocaine, salts thereof, and mixtures thereof.

* * * * *